(12) United States Patent
Zhang et al.

(10) Patent No.: US 10,215,666 B2
(45) Date of Patent: Feb. 26, 2019

(54) SAMPLE INJECTION DEVICE AND METHOD FOR SAMPLE COLLECTION AND SAMPLE THERMAL DESORPTION, AND TRACE DETECTION APPARATUS

(71) Applicant: Nuctech Company Limited, Haidian District, Beijing (CN)

(72) Inventors: Qingjun Zhang, Beijing (CN); Yuanjing Li, Beijing (CN); Zhiqiang Chen, Beijing (CN); Weiping Zhu, Beijing (CN); Huishao He, Beijing (CN); Qiufeng Ma, Beijing (CN); Yaohong Liu, Beijing (CN); Xiang Zou, Beijing (CN); Jianping Chang, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 159 days.

(21) Appl. No.: 15/117,086

(22) PCT Filed: Dec. 28, 2015

(86) PCT No.: PCT/CN2015/099185
§ 371 (c)(1),
(2) Date: Aug. 5, 2016

(87) PCT Pub. No.: WO2016/107515
PCT Pub. Date: Jul. 7, 2016

(65) Prior Publication Data
US 2017/0176299 A1    Jun. 22, 2017

(30) Foreign Application Priority Data

Dec. 31, 2014   (CN) .......................... 2014 1 0852020

(51) Int. Cl.
*G01N 1/02* (2006.01)
*G01N 30/08* (2006.01)
(Continued)

(52) U.S. Cl.
CPC ............. *G01N 1/02* (2013.01); *G01N 1/2211* (2013.01); *G01N 1/2214* (2013.01);
(Continued)

(58) Field of Classification Search
None
See application file for complete search history.

(56) References Cited

U.S. PATENT DOCUMENTS 4,128,008 A  *  12/1978  Linenberg .............. G01N 1/405
                                                  73/863.12
4,849,179 A  *   7/1989  Reinhardt .............. G01N 30/08
                                                  422/89
(Continued)

FOREIGN PATENT DOCUMENTS

CN      1296564 A      5/2001
CN      2570784 Y      9/2003
(Continued)

OTHER PUBLICATIONS

Japanese Office Action for corresponding Japanese Patent Application No. 2016-532073 dated Apr. 24, 2017, 5 pgs.
(Continued)

*Primary Examiner* — Paul M. West
*Assistant Examiner* — Mark A Shabman
(74) *Attorney, Agent, or Firm* — Merchant & Gould P.C.

(57) ABSTRACT

A sample injection device for sample collection and thermal desorption includes: a sample collection structure; a piston type adsorber having an adsorption cavity communicating with the sample collection structure; a piston cylinder defining a piston chamber accommodating the adsorber and
(Continued)

communicating with the adsorption cavity; a thermal desorption chamber communicating with the adsorption cavity and the piston chamber; and a pump configured to pump a sample diffused in an ambient gas into the adsorption cavity through the sample collection structure and the piston chamber; the adsorber is movable between a sample collecting position where the adsorption cavity is outside the thermal desorption chamber and adsorbs the sample collected by the sample collection structure and a sample desorbing position where the adsorption cavity is inside the thermal desorption chamber so that the adsorbed sample is thermally desorbed in the thermal desorption chamber.

20 Claims, 3 Drawing Sheets

(51) Int. Cl.
```
    G01N 1/22    (2006.01)
    G01N 1/40    (2006.01)
    G01N 27/62   (2006.01)
    H01J 49/04   (2006.01)
    G01N 1/42    (2006.01)
    G01N 1/38    (2006.01)
    G01N 30/12   (2006.01)
```
(52) U.S. Cl.
    CPC .......... G01N 1/2273 (2013.01); G01N 1/405 (2013.01); G01N 27/622 (2013.01); G01N 30/08 (2013.01); H01J 49/0422 (2013.01); H01J 49/0459 (2013.01); H01J 49/0468 (2013.01); *G01N 1/38* (2013.01); *G01N 1/42* (2013.01); *G01N 2030/128* (2013.01)

(56) References Cited

U.S. PATENT DOCUMENTS

| | | | | |
|---|---|---|---|---|
| 5,970,804 | A * | 10/1999 | Robbat, Jr. | G01N 1/405 73/23.41 |
| 6,134,945 | A * | 10/2000 | Gerstel | B01D 53/30 422/78 |
| 7,449,050 | B2 * | 11/2008 | Wohltjen | B01D 53/0407 422/88 |
| 7,730,796 | B2 * | 6/2010 | Shimada | G01N 1/2214 73/863.12 |
| 7,977,113 | B2 * | 7/2011 | Donaldson | G01N 1/2202 422/401 |
| 2004/0235025 | A1 * | 11/2004 | Mori | B01L 3/0275 435/6.13 |
| 2009/0050801 | A1 * | 2/2009 | Fedorov | H01J 49/066 250/288 |
| 2009/0255322 | A1 * | 10/2009 | Nishino | G01N 30/12 73/23.41 |
| 2009/0272894 | A1 * | 11/2009 | Shiokawa | H01J 49/145 250/282 |
| 2012/0223226 | A1 * | 9/2012 | Rafferty | G01N 1/405 250/288 |

FOREIGN PATENT DOCUMENTS

| | | |
|---|---|---|
| CN | 101294933 A | 10/2008 |
| CN | 101672833 A | 3/2010 |
| CN | 101900706 A | 12/2010 |
| CN | 201935894 U | 8/2011 |
| CN | 102455318 A | 5/2012 |
| CN | 102478466 A | 5/2012 |
| CN | 202471497 U | 10/2012 |
| CN | 104569228 A | 4/2014 |
| CN | 204302250 U | 4/2014 |
| CN | 103852370 A | 6/2014 |
| CN | 104483423 A | 4/2015 |
| CN | 204314263 U | 5/2015 |
| EP | 1 434 050 A1 | 6/2004 |
| EP | 2 746 755 A1 | 6/2014 |
| JP | S59-025453 U | 2/1984 |
| JP | H02-115742 A | 4/1990 |
| JP | H05-500114 A | 1/1993 |
| JP | 2004-251809 A | 9/2004 |
| JP | 2005-291921 A | 10/2005 |
| JP | 2007-212325 A | 8/2007 |
| JP | 2009-236589 A | 10/2009 |
| RU | 2102742 C1 | 1/1998 |
| WO | 2013/021067 A1 | 2/2013 |

OTHER PUBLICATIONS

International Search Report for corresponding International Patent Application No. PCT/CN2015/099185 dated Mar. 24, 2016, 3 pgs.
Chinese Office Action for corresponding Chinese Patent Application No. 201410852020.1 dated Oct. 10, 2015, 7 pgs.
Delcourt, J. et al., "Thermal Desorption—Possibilities and Limitations", Chromatographia, 17(2): 88-92 (1983).
Hong, P. et al., "A Cryogen-free Refrigerating Prconcentration/Thermal Desorption Instrument for On-line Determination of Volatile Organic Compounds in Ambient Air", Chinese Journal of Analytical Chemistry, 1483-1486 (2011), English Abstract.
Jia, J. et al., "A Rapid Sample Introduction Method of Thermal Desorption for Ion Mobility Spectrometer", State Key Laboratory of Transducer Technology, Institute of Electronics, Chinese Academy of Sciences (2011), 4 pgs., English Abstract.
Lawrence, A.H., "Detection of Drug Residues on the Hands of Subjects by Surface Sampling and Ion Mobility Spectrometry", Forensic Science International, 34: 73-83 (1987).
Extended European Search Report for corresponding European Patent Application No. 15860000.7 dated Aug. 6, 2018, 20 pages.

* cited by examiner

SAMPLE INJECTION DEVICE AND METHOD FOR SAMPLE COLLECTION AND SAMPLE THERMAL DESORPTION, AND TRACE DETECTION APPARATUS

This application is a National Stage Application of PCT/CN2015/099185, filed 28 Dec. 2015, which claims benefit of Serial No. 201410852020.1, filed 31 Dec. 2014 in China and which applications are incorporated herein by reference. A claim of priority is made to each of the above disclosed applications.

BACKGROUND OF THE INVENTION

Field of the Invention

Embodiments of the present invention generally relate to the field of safety detection technology, and in particular, to sample injection device and method for sample collection and sample thermal desorption, and a trace detection apparatus, which are capable of performing real-time collection and pre-concentration of volatile substance, semi-volatile substance, surface contaminant or the like, and which are suitable for fast sample collection and injection for Gas Chromatograph (GC), Ion Mobility Spectrometry (IMS), Gas Chromatography-Ion Mobility Spectrometry (GC-IMS) combination spectrometer or the like.

Description of the Related Art

Ion Mobility Spectrometry (IMS) technology has advantages of simple structure, high sensitivity, and fast analysis speed. It is able to achieve a fast trace (in ppb order of magnitude) detection on a substance under atmospheric pressure or near atmospheric pressure, and is very suitable for in-field use. Accordingly, IMS is widely applied for detection or inspection in various aspects including toxic chemical, narcotic drugs, explosives, environments, etc. However, during detection of mixtures, the IMS, as a detection instrument alone, encounters the following problems: (1) due to problems on the manufacturing process, currently commercial IMS only has a resolution ratio of about 30, which is difficult in differentiating chemical compounds having similar migration rates from one another; (2) ions from some chemical compounds undergo complicate reaction and annihilate each other in the ionization zone; (3) the IMS has a relatively lower dynamic range, so that, when there is/are one or several type(s) of chemical compounds with greatly large concentration(s), generations of ions of other types of chemical compounds will be adversely affected, which results in missed detection. Based on the above reasons, it is prone to trigger of false alarm or failing of alarm when a complex mixture having many types of chemical compounds is detected by the IMS.

Gas chromatography—ion mobility spectrometry (GC-IMS) combination technology has an excellently separation ability on complicated sample, and is capable of performing a pre-separation on the mixture, to separate the mixture into single components to be detected by the IMS. This combination technology will greatly enhance accuracy of the detection on the mixture. Conventional GC's analysis time is in order of magnitude of ten minutes or more, so it is difficult to meet demands on on-site fast detection. In recent years, fast GC technology has been developed rapidly, and its separation time (of tens of seconds—minutes) is greatly shortened compared to conventional GC. Fast GC-IMS, on one hand, inherits the separation ability of the GC, and on the other hand, succeeds to high sensitivity, fast response speed characteristics of the IMS, accordingly, it is capable of detecting complex components of the sample with a detection limit that is superior to the ppb order of magnitude and a detection time from a few minutes to tens of minutes. In addition, the fast GC-IMS reflects full advantages in the aspects of miniaturization and portable, is very suitable for on-site fast detection of a sample including complex components. This technology will play a powerful role in fields including anti-terrorism and riot control, drug smudging, environmental monitoring, food safety, and so on.

Sample injector is an integral part of a trace analytical instrument. Main sampling modes for a separate IMS comprise a wipe sampling thermal desorption mode and a direct sampling thermal desorption mode. The wipe sampling mode generally includes: wiping a substance to be detected by using a high temperature resistant wiping paper with a certain flexibility, and then, the sampling paper is put into a slot of the thermal desorption sample injector so that the substance adhered to the sampling paper is thermally desorbed by heating. This mode is only suitable for the sampling on surface contaminants, but is not suitable for the direct sampling on volatile or semi-volatile substances. In addition, the GC has sample injection requirements, which are different from those of the IMS, including rapid gasification of the sample's components, and rapid, accurate and quantitative application on the GC's column head after being mixed with the carrier gas. Accordingly, the existing IMS sample injection methods are not suitable for the GC-IMS in principle or in the sampling efficiency.

For a conventional GC sample injector, split/splitless sampling modes are used generally for solution samples; in these modes, however, not only interference of sample matrix on analysis needs to be considered, but also interference of sample solvents on analysis needs to be considered. Meanwhile, the sample further needs to be subject to a complicated pre-treatment, which is not suitable for on-site fast detection. Although a currently widely used head space sample injection does not require a complicated pre-treatment, it still "destructively" obtains a certain amount of sample, so it is not suitable for fast on-site detection for the trace gas without unpacking.

In a word, conventional IMS and GC technologies have low efficiency in sample collection and sample injection, low collection speed, and requires unpacking, which is not suitable for fast GC-IMS on-site detection.

SUMMARY

In order to overcome at least one of the abovementioned problems and defects existing in the prior art, the present invention is provided.

According to an aspect of the present invention, there is provided a sample injection device for sample collection and sample thermal desorption, comprising: a sample collection structure; a piston type adsorber having an adsorption cavity that is capable of being arranged to be in communication with the sample collection structure; a piston cylinder defining a piston chamber that is configured for accommodating the piston type adsorber and configured to be in communication with the adsorption cavity; a thermal desorption chamber that is configured to be in communication with the adsorption cavity and the piston chamber and is configured to thermally desorb the sample adsorbed in the adsorption cavity; and a pump that is configured to be in communication with the piston chamber via a conduit and is configured to pump a sample diffused in an ambient gas into the adsorption cavity through the sample collection structure, the adsorption cavity being configured to adsorb the sample collected by the sample collection structure; wherein the piston type adsorber is configured to be movable between a sample collecting position where the adsorption cavity is located outside the thermal desorption chamber and in communication with the sample collection structure so as to adsorb the sample collected by the sample collection structure and a sample desorbing position where the adsorption cavity is located inside the thermal desorption chamber so that the adsorbed sample is thermally desorbed in the thermal desorption chamber.

In the above sample injection device for sample collection and sample thermal desorption, the sample collection structure may comprise a sample collection opening, a filter structure mounted onto or over the sample collection opening and a connection tube connecting the sample collection opening to the piston cylinder; and the piston cylinder may comprise a cylinder body that is mounted to the thermal desorption chamber and is provided with a sampling connection gas nipple being in communication with the piston chamber, and one end of the connection tube is configured to be mounted hermetically and detachably to the sampling connection gas nipple.

In the above sample injection device for sample collection and sample thermal desorption, a desiccant for adsorption of moisture in the sample may be placed within the connection tube.

In the above sample injection device for sample collection and sample thermal desorption, at least a portion of the connection tube comprises a retractable hose.

In the above sample injection device for sample collection and sample thermal desorption, the piston type adsorber may comprise a piston rod body and the adsorption cavity connected to a distal end of the piston rod body, and the adsorption cavity comprises a net-like structure filled with adsorbents therein.

In the above sample injection device for sample collection and sample thermal desorption, the adsorption cavity may comprise an adsorption passage configured to be in communication with the sample collection structure to receive the collected sample when the piston type adsorber is located at the sample collecting position.

In the above sample injection device for sample collection and sample thermal desorption, the piston type adsorber may further comprise a thermal insulation pad detachably connected to one end of the adsorption cavity away from the piston rod body.

In the above sample injection device for sample collection and sample thermal desorption, the piston rod body may comprise a cooling passage and a plurality of through holes formed in a lower part of the piston rod body; the cooling passage may be configured to be in direct communication with the ambient gas when the piston type adsorber is located at the sample collecting position, and in communication with the ambient gas via a cooling through hole formed in the piston cylinder when the piston type adsorber is located at the sample desorbing position, and the plurality of through holes are configured to be in communication with the cooling passage and the piston chamber.

The above sample injection device may further comprise a plurality of sealing rings provided around the piston type adsorber such that the piston type adsorber is hermetically accommodated within the piston cylinder.

In the above sample injection device for sample collection and sample thermal desorption, the piston cylinder may comprise a guide rail provided within the thermal desorption chamber to guide a movement of the piston type adsorber within the thermal desorption chamber.

In the above sample injection device for sample collection and sample thermal desorption, the thermal desorption chamber may comprise a chamber body and a liner provided on an inner wall of the chamber body, and an outer wall of the chamber body may be covered with a heating structure.

In the above sample injection device for sample collection and sample thermal desorption, the thermal desorption chamber may be further provided with a carrier gas inlet, a gas outlet and an analyzer interface.

The above sample injection device may further comprise a thermal insulation structure provided between the piston cylinder and the thermal desorption chamber. O-rings may be provided among the three components, to form a hermetical desorption chamber.

According to another aspect of the present invention, there is provided a trace detection apparatus comprising: the abovementioned sample injection device for sample collection and sample thermal desorption; and a sample analyzer connected to the sample injection device.

According to still another aspect of the present invention, there is provided a method of collecting and desorbing a sample by using the abovementioned sample injection device, the method comprising steps of: positioning the piston type adsorber into the sample collecting position so that the adsorption cavity is in communication with the sample collection structure; pumping a sample diffused in the ambient gas into the adsorption cavity through the sample collection structure by starting up the pump; maintaining a temperature inside thermal desorption chamber at a constant high temperature by using a thermal desorption temperature-controlling system; and moving and positioning the piston type adsorber into the sample desorbing position so that the adsorption cavity is located within the thermal desorption chamber and the sample adsorbed within the adsorption cavity is thermally desorbed within the thermal desorption chamber at the high temperature.

In the abovementioned method, the pump may be kept working to continuously pump the sample and to preconcentrate the sample within the adsorption cavity.

In the abovementioned method, during the sample adsorbed by the adsorption cavity being thermally desorbed within the thermal desorption chamber at high temperature, the pump may be started up to pump gas so that a portion of the piston type adsorber outside the thermal desorption chamber is kept at a room temperature.

Other objects and advantages of the present invention will become apparent and more readily appreciated from the following detailed description of the present invention, taken in conjunction with accompanying drawings.

BRIEF DESCRIPTION OF THE DRAWINGS

Features and advantages of the present invention will be more readily appreciated with respect to the accompanying drawings, which are illustrative and should not be construed as limitations to the present invention, and in which.

DETAILED DESCRIPTION OF THE EMBODIMENTS

Technical solutions of the present invention will be described hereinafter clearly and completely in embodiments with reference to the attached drawings. Obviously, the illustrated embodiments are some of embodiments of the present invention, rather than being construed as all of embodiments of the present invention. Based on the described embodiments of the present invention, any others embodiments obtained by those skilled in the art without inventive labor fall into the scope of the present invention.

In addition, in the following detailed description, for purposes of explanation, numerous specific details are set forth in order to provide a thorough understanding of the embodiments of the present disclosure. It will be apparent, however, that one or more embodiments may be practiced without these specific details. In other instances, well-known structures and devices are schematically shown in order to simplify the drawing.

According to a general concept of the present invention, there is provided a sample injection device for sample collection and sample thermal desorption comprising: a sample collection structure; a piston type adsorber having an adsorption cavity that is capable of being arranged to be in communication with the sample collection structure and configured to adsorb the sample collected by a sample collection structure; a piston cylinder defining a piston chamber that is configured for accommodating the piston type adsorber and configured to be in communication with the adsorption cavity; a thermal desorption chamber that is configured to be in communication with the adsorption cavity and the piston chamber and is configured to thermally desorb the sample adsorbed in the adsorption cavity; and a pump that is configured to be in communication with the piston chamber via a conduit and is configured to pump a sample diffused in an ambient gas into the adsorption cavity through the sample collection structure; wherein the piston type adsorber is configured to be movable between a sample collecting position where the adsorption cavity is located outside the thermal desorption chamber and in communication with the sample collection structure so as to adsorb the sample collected by the sample collection structure and a sample desorbing position where the adsorption cavity is located inside the thermal desorption chamber so that the adsorbed sample is thermally desorbed in the thermal desorption chamber.

Figure 1:
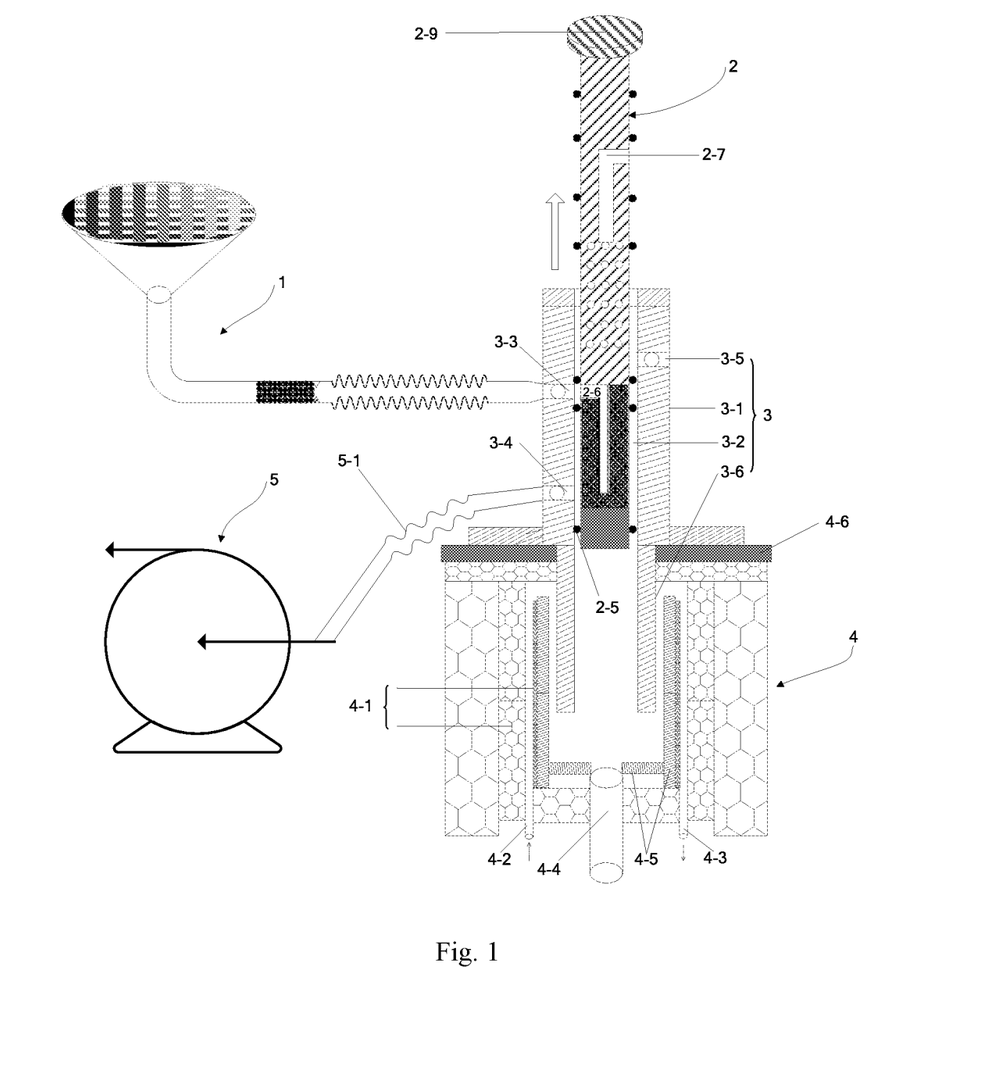
FIG. 1 is a block diagram schematically showing configuration of a sample injection device for sample collection and sample thermal desorption according to an exemplary embodiment of the present invention, in a sample collecting state.

FIG. 1 schematically shows a configuration of a sample injection device for sample collection and sample thermal desorption according to an exemplary embodiment of the present invention. As shown, the sample injection device for sample collection and sample thermal desorption mainly comprises a sample collection structure 1, a piston type adsorber 2, a piston cylinder 3, a thermal desorption chamber 4 and a pump 5. Structures and operations of these components will be described in detail hereafter.

Figure 2:
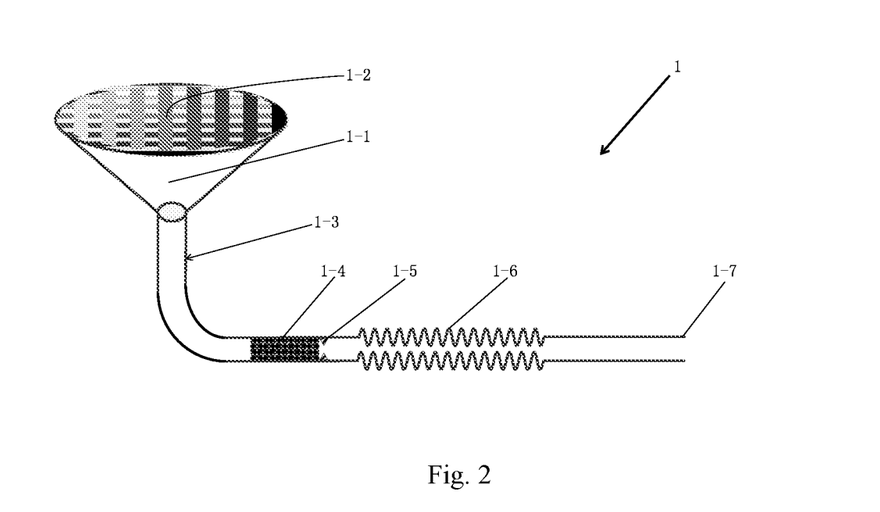
FIG. 2 shows schematically an example of arrangement of a sample collection structure in the sample injection device for sample collection and sample thermal desorption shown in FIG. 1.

FIG. 2 shows schematically an example of a sample collection structure according to the present invention. In FIG. 2, the sample collection structure 1 mainly comprises a sample collection opening 1-1, a filter structure 1-2 mounted to the sample collection opening 1-1, and a connection tube 1-3 connecting the sample collection opening 1-1 with the piston cylinder 3. The sample collection opening 1-1 may have a trumpet shape, and will be placed in an ambient gas where a sample to be collected is leaked or where a sample having surface contaminants is present during sampling, thereby effectively enlarging a sample collecting area and facilitating fast collection of the sample. The filter structure 1-2, such as a filter screen, mounted to a front end of the sample collection opening 1-1, may prevent the tube from being blocked due to entrance of large particulate matter(s). The sample collection opening 1-1 is connected to and in communication with the piston cylinder 3 through the connection tube 1-2.

Desiccant 1-4, which is able to adsorb water and moisture contained in the collected sample during the sample collection, may be placed within the connection tube 1-2, in order to protect the chromatographic column and the migration tube of the analytic instrument. The desiccant may be contained in a desiccant bag. Structure 1-5 for fixation of the desiccant or the desiccant bag, such as a protrusion, may be provided in the connection tube, preventing movement of the desiccant or the desiccant bag under the pumping action of the pump.

At least a portion of the connection tube 1-2, such as a portion after the desiccant, comprises a retractable hose or bellows 1-6. This retractable hose or bellows 1-6 may be stretched and/or rotated during sampling, to adjust an orientation of the sample collection opening 1-1, thereby greatly facilitating the sample collection implemented by a user. A distal end 1-7 of the connection tube 1-2 is configured for being connected hermetically and detachably to the piston cylinder 3.

Figure 3:
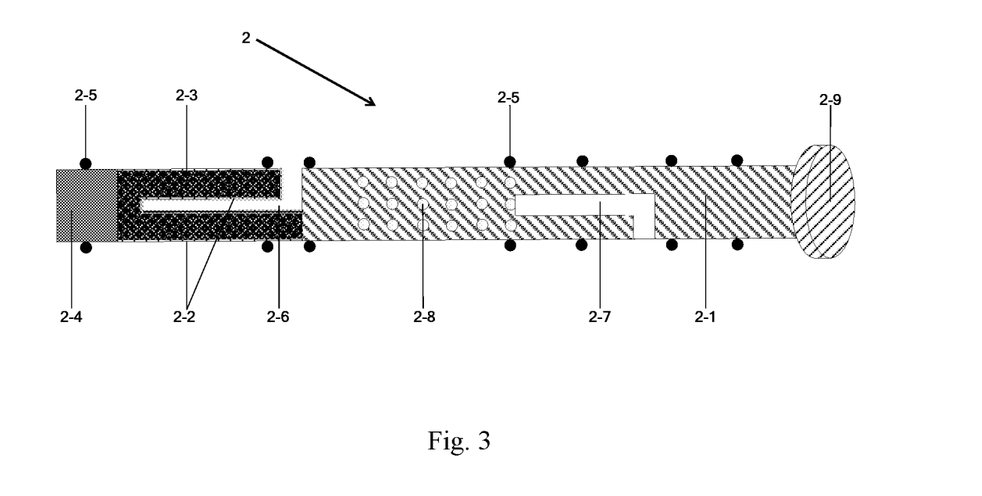
FIG. 3 shows schematically an example of arrangement of a piston type adsorber in the sample injection device for sample collection and sample thermal desorption shown in FIG. 1.

FIG. 3 shows schematically an example of a piston type adsorber according to the present invention. As shown, the piston type adsorber 2 is in a form of wholly cylindrical piston that may be reciprocated within the piston cylinder 3, and mainly comprises a piston rod body 2-1 and an adsorption cavity 2-2 connected to a distal end of the piston rod body 2-1. The piston rod body 2-1 may be made of a chemically stable heat resistant material, such as PTFE.

In an example, the adsorption cavity 2-2 may comprise a net-like structure filled with adsorbents 2-3 therein, that is, mesh holes are formed in walls of the cavity and the adsorbents 2-3 are filled within the cavity. Adsorbent materials having different adsorption characteristics may be added selectively in accordance with different detection demands. Such on-demand selection enhances selective adsorption on the sample to be detected, to a certain extent. It will be understood that, a diameter of the adsorbent filled should be greater than a size or diameter of the mesh hole. Referring to FIG. 3, the adsorption cavity 2-2 may be in a partially hollow form, that is, it may comprise an adsorption passage 2-6, which is L-shaped or walking stick-shaped and has an opening in the wall of the cavity. As described hereafter, the adsorption passage is configured to be in communication with the sample collection structure during sampling, so as to receive the sample adsorbed via the connection tube 1-3. As a result, not only the sample will enter the adsorbents easily, but also a contact area between the sample and the adsorbents is increased, which helps adsorption of the sample.

In an example, the piston rod body 2-1 may comprise a cooling passage 2-7 and a plurality of through holes 2-8 formed in a lower part of the piston rod body. As described hereafter, the cooling passage 2-7 is configured to be in direct communication with the ambient gas when the piston type adsorber is located at the sample collecting position, and to be in communication with the ambient gas through a cooling through hole formed in the piston cylinder when the piston type adsorber is located at the sample desorbing position. The cooling passage 2-7 may also be L-shaped or walking stick-shaped and have an opening to the ambient gas. The through holes 2-8 are configured to communicate with the cooling passage 2-7 and interior of the piston chamber 3. This hollow piston rod body, on one hand, will reduce mass of the piston type adsorber and facilitate rapid heating and cooling of the adsorber, and on the other hand, may communicate the pump 5 with a cooling gas inlet 3-5 at an upper part of the piston cylinder 3 (see FIGS. 1 and 4) during sample injection, such that he upper part of the adsorber may be air-cooled by pumping of the pump, which speeds up a cooling rate at the upper part of the piston type adsorber and helps to rapidly cool down the adsorption cavity at the lower part of the piston type adsorber together with the adsorbents therein, facilitating adsorption of the sample.

According to an embodiment of the present invention, the piston type adsorber 2 may further comprise a thermal insulation pad 2-4 detachably connected to one end of the adsorption cavity 2-2 away from the piston rod body 2-1. That is, the adsorption cavity 2-2 is disposed between the piston rod body 2-1 and the thermal insulation pad 2-4. Exemplarily, the piston type adsorber may be pulled out or the piston cylinder may be unscrewed, and then the thermal insulation pad located at bottom of the adsorber is unscrewed and removed, so that the adsorbents within the adsorption cavity may be replaced. The thermal insulation pad may be made of a PTFE material. Provision of the thermal insulation pad will reduce thermal transmission from the thermal desorption chamber to the adsorption cavity, effectively ensuring that the adsorption cavity as well as the adsorbents is kept cool, e.g., at near room temperature, during sampling/collection at the piston type adsorber, facilitating adsorption and collection of the sample.

Figure 4:
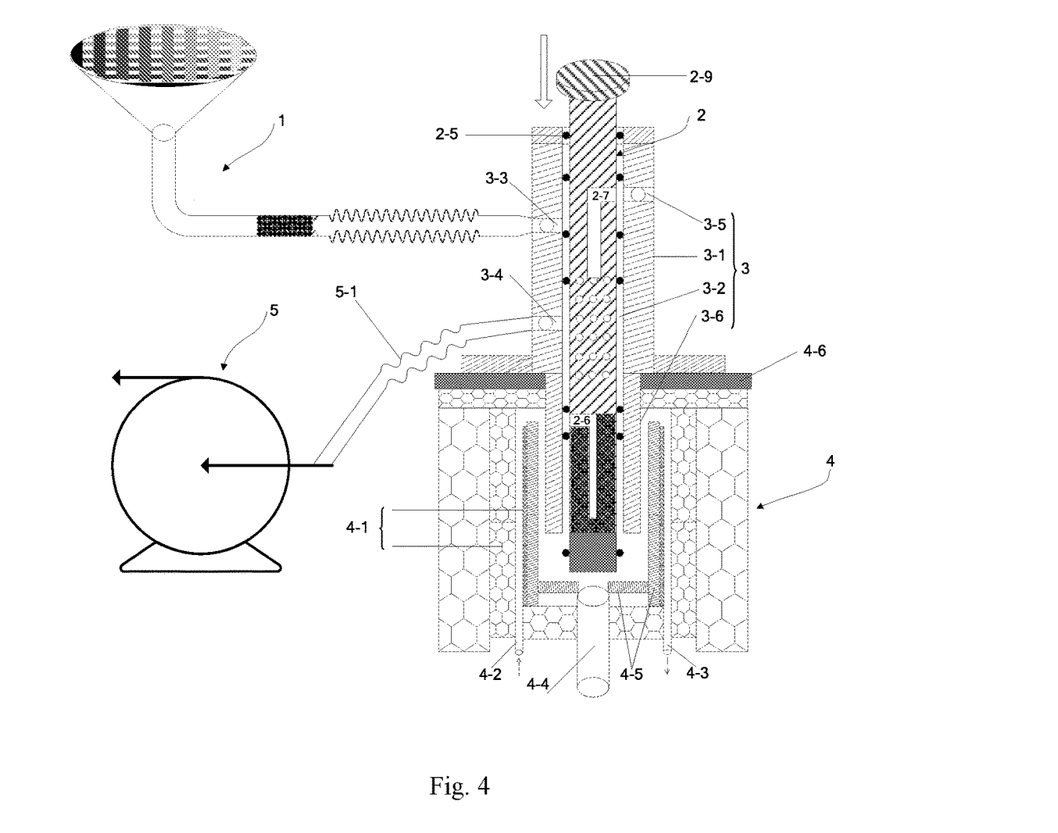
FIG. 4 is a block diagram schematically showing configuration of a sample injection device for sample collection and sample thermal desorption according to an exemplary embodiment of the present invention, in a sample desorbing and injection state.

In an embodiment, a plurality of sealing rings 2-5 is fitted over the piston type adsorber 2, such as over an outer surface of the piston type adsorber 2, such that the piston type adsorber 2 is hermetically received in the piston cylinder 3. Preferably, the sealing rings 2-5 are arranged such that when the piston type adsorber 2 reciprocates between a highest position (for example, a sample collecting position) and a lowest position (for example, a sample desorbing position) within the piston cylinder 3, the piston type adsorber 2 is kept in a seal contact with an inner wall of the piston cylinder 3 via the sealing rings 2-5, as shown in FIGS. 1 and 4. Exemplarily, some of the sealing rings 2-5 are disposed at positions near the opening of the adsorption passage 2-6 and at positions near the opening of the cooling passage 2-7, as shown in FIG. 3.

A push-and-pull handle 2-9 may be disposed at a distal end of the piston rod body 2-1 of the piston type adsorber 2, and is configured for moving the piston type adsorber 2 reciprocally within the piston cylinder 3 by means of push and pull actions implemented by the user.

Referring to FIGS. 1 and 4, the piston cylinder 3 mainly comprises a cylinder body 3-1, and a piston chamber 3-2 for receiving the piston type adsorber 2 and being in communication with the adsorption cavity 2-2. The cylinder body 3-1 may be made of PTFE material having high strength, good heat resistance and stable chemical properties, and defines at least a portion of the piston chamber 3-2. The cylinder body 3-1 is mounted on the thermal desorption chamber 4 and is provided with a sampling connection gas nipple 3-3 in communication with the piston chamber 3-2. As mentioned above, a distal end of the connection tube 1-3 of the sample collection structure 1 may be mounted or inserted hermetically and detachably to the sampling connection gas nipple 3-3, so that a communication between an inner sample passage of the sample collection structure 1 and the piston chamber 3-2 is achieved. A valve for controlling on/off of this communication may be provided in the sampling connection gas nipple 3-3.

The cylinder body 3-1 is further provided with a pump connection gas nipple 3-4, and the pump 5 is connected to the gas nipple 3-4 through a conduct 5-1 so as to be in communication with the piston chamber 3-2. As such, during the sampling/collection or pre-concentration, the pump 5, the conduit 5-1, the pump connection gas nipple 3-4, the piston chamber 3-2, the sampling connection gas nipple 3-3, the connection tube 1-3, and the sample collection opening 1-1 constitute a communication path. Once the pump 5 is started-up, a sample to be sampled (e.g., volatile or semi-volatile substance, or surface contaminants) contained in the ambient gas will be pumped into the adsorption cavity 2-2, and is adsorbed/pre-concentrated in the adsorption cavity 2-2. During sampling, the pump 5 works continuously so that the sample is adsorbed/pre-concentrated in the adsorption cavity. During sampling, the whole piston type adsorber is kept at room temperature.

The piston cylinder 3 may further comprise a guide rail 3-6 provided within the thermal desorption chamber 4 to guide a movement of the piston type adsorber 2 within the thermal desorption chamber 2, thereby effectively preventing the piston type adsorber 2 from shaking, and improving degree of the firmness. The guide rail 3-6 is connected to the cylinder body 3-1 and defines a portion of the piston chamber 3-2. Form of the guide rail 3-6 is not limited. In an example, there may be two parallel rod-like rails, or the guide rail may be in a cylindrical form.

Referring to FIGS. 1 and 4, the thermal desorption chamber 4 mainly comprises a chamber body 4-1, and an internal space defined by the chamber body 4-1 and adapted for thermal desorption of the sample. The chamber body 4-1 is formed with a carrier gas inlet 4-2, a shunting and/or sweeping gas outlet 4-3, and an interface 4-4 for connection to an analytical instrument such as chromatographic column, IMS or the like.

A liner 4-5 having stable chemical performance may be embedded hermetically in the chamber body of the thermal desorption chamber 4 and will effectively prevent a direct contact between the sample and a metallic wall of the thermal desorption chamber. The liner 4-5 may be replaced regularly, which can avoid a direct pollution of the thermal desorption chamber by the sample, reduce a sample distortion rate, and enhance accuracy and reliability of the sample detection. An outer wall of the chamber body of the thermal desorption chamber 204 may be provided with a heating structure or a heating film, for heating the thermal desorption chamber 4. The thermal desorption chamber 3-10 may be provided with a temperature sensor, for example on the outer surface of the chamber body, for real time detecting and monitoring the temperature within the thermal desorption chamber. In addition, the outer wall of the chamber body of the thermal desorption chamber 204 may be covered with a thermal insulation cotton for thermally insulating the thermal desorption chamber, so as to reduce the power consumption. The heating structure, the temperature sensor and/or the thermal insulation cotton are components of a thermal desorption temperature controlling system, which keep the temperature of the thermal desorption chamber at a constant temperature, e.g., 80° C.~300° C., under the control of a controller. The thermal desorption chamber may adopt a programmed heating mode, which reduces the power consumption.

Thermal insulation structure 4-6, for example, porous ceramic thermal insulation disc, may be provided or inserted between the thermal desorption chamber 204 and the piston cylinder 203, and can effectively insulate a heat exchange between the thermal desorption chamber and the upper part of the piston type adsorber (e.g., the piston rod body) during desorption of the sample, and can also effectively insulate a heat exchange between the thermal desorption chamber and the piston type adsorber and a heat exchange between the thermal desorption chamber and the upper part of the piston cylinder during collection of the sample. This ensures the whole piston type adsorber is kept at the room temperature during collection of the sample, facilitating collection of the sample.

When it is needed to thermal desorb the sample, the thermal desorption temperature controlling system is operated firstly to maintain the temperature in the thermal desorption chamber at a suitably constant high temperature (80° C.~300° C.). The piston type adsorber adsorbed with the sample is pushed quickly into the thermal desorption chamber at the high temperature. The adsorbents pushed into the thermal desorption chamber are heated rapidly so that the sample adsorbed in the adsorption cavity will be thermal desorbed instantly at the high temperature. The desorbed sample will be mixed with preheated carrier gas introduced the carrier gas inlet of the thermal desorption chamber through, and finally is taken by the carrier gas into the detection device or the analytical instrument for detection or analysis.

As described above, the pump 5, the piston chamber 3-2, the plurality of through holes 2-8 formed in the piston rod body, the cooling passage 2-7, and the cooling air inlet 3-5 formed in the piston cylinder 3 constitute a communication path while the adsorption cavity is pushed into the thermal desorption chamber. Accordingly, the upper part (including the piston rod body) of the piston type adsorber outside the thermal desorption chamber will be air cooled by the air exhaust operation of the pump 5, which facilitates a next sample adsorption and enrichment or pre-concentration.

This sample injection device for sample collection and sample thermal desorption has the sample enrichment or pre-concentration function and thus may be used directly as an IMS instrument or GC, or be served as a sample injector for chemical substance trace analytical instruments including IMS-GC, GC-MS, etc., and it needs not to give unnecessary details herein.

Operations of the abovementioned sample injection device for sample collection and sample thermal desorption will be described hereafter with reference to FIG. 1 and FIG. 4. First of all, the piston type adsorber 2 is pulled to be positioned at the sample collecting position as shown in FIG. 1, such that the adsorption cavity 2-2 is in communication with the sample collection structure 1. At this time, the pump 5, the conduit 5-1, the pump connection gas nipple 3-4, a portion of the piston chamber 3-2 (including the portion surrounding the adsorption cavity), the sampling connection gas nipple 3-3, the connection tube 1-3 and the sample collection opening 1-1 constitute a communication path by means of the sealing rings 2-5. Then, the pump 5 is started up, so that a sample to be sampled (for example, volatile substances, semi-volatile substances or surface contaminants) in the ambient gas is suctioned into the adsorption cavity 2-2, and is adsorbed/pre-concentrated in the adsorption cavity 2-2. During sampling, the pump 5 may operate continuously so that the sample is enriched or pre-concentrated within the adsorption cavity. During the sampling, the whole piston type adsorber may be kept at a room temperature.

After that, the thermal desorption temperature controlling system is started up, so that the temperature of the thermal desorption chamber 4 is kept at a constant high temperature. Then, the piston type adsorber 2 is moved rapidly to be positioned at the sample desorbing position as shown in FIG. 4, so that the adsorption cavity 2-2 is positioned within the thermal desorption chamber 4. The adsorption cavity 2-2 may be sealed by the sealing rings 2-5 within the lower part of the piston chamber 3-2, so that it is sealed within the thermal desorption chamber 4. Here, the adsorbents that are pushed into the thermal desorption chamber 4 are heated up rapidly so that the sample adsorbed in the adsorption cavity 2-2 is desorbed instantly at high temperature. The desorbed sample is mixed with a pre-heated carrier gas 4-2 imported from the carrier gas inlet 4-2 of the thermal desorption chamber 4, and finally, is brought by the carrier gas into a detection device or analytical instrument (not shown), for detection or analysis.

During desorption of the sample within the thermal desorption chamber, the pump 5, the conduit 5-1, the pump connection gas nipple 3-4, a portion of the piston chamber 3-2 (namely the portion outside the thermal desorption chamber 4), the plurality of through holes 2-8 formed in the piston rod body 2-1, the cooling passage 2-7, and the cooling air inlet 3-5 in the piston cylinder 3 constitute a path or space that is in communication with the ambient gas. Accordingly, the upper half part of the piston type adsorber 2 outside the thermal desorption chamber 4 is air-cooled by the suction function of the pump 5, so that temperature of the part of the piston type adsorber positioned outside the thermal desorption chamber is maintained at a room temperature, facilitating a next sample adsorption and enrichment or pre-concentration.

With the abovementioned sample injection device for sample collection and sample thermal desorption according to the embodiments of the present invention, samples of volatile or semi-volatile substances or surface contaminants may be obtained by performing direct sample adsorption and collection on a surface to be detected or in the ambient gas atmosphere. The obtained sample may be thermally desorbed within the thermal desorption chamber, and then is brought by the carrier gas into a chromatograph or IMS spectrometer for detection or analysis. With the abovementioned sample injection device for sample collection and sample thermal desorption, the sample will be pre-concentrated or enriched in the adsorption cavity or onto the adsorbents therein by a continuous pumping operation of a suction pump. Pre-concentration of the sample may lower the requirements on a lower detection limit of the detector such as IMS and the like, and reduce difficulty and cost of instrument development. Meanwhile, with the abovementioned sample injection device for sample collection and sample thermal desorption, self air suction and cooling will be achieved, which facilitates a next sample adsorption and collection or pre-concentration. The sample injection device of the present invention integrates sample collection, pre-concentration and thermal desorption functions, needs no external head space equipment, requires no preparation of solution and no unpacking for sampling, saves space and time, facilitates miniaturization and portable development of the instrument, increases the throughput of the instrument, and, is very advantageous to on-site rapid detections at airport, customs and so on.

Although these embodiments of the present invention have been shown and described, it would be appreciated by those skilled in the art that various changes or modifications may be made in these embodiments without departing from the principles and spirit of the present invention, the scope of which is defined in the claims and their equivalents.

What is claimed is:

1. A sample injection device for sample collection and sample thermal desorption, comprising:
   a sample collection structure;
   a piston type adsorber having an adsorption cavity that is capable of being arranged to be in communication with the sample collection structure;
   a piston cylinder defining a piston chamber that is configured for accommodating the piston type adsorber and configured to be in communication with the adsorption cavity;
   a thermal desorption chamber that is configured to be in communication with the adsorption cavity and the piston chamber and is configured to thermally desorb the sample adsorbed in the adsorption cavity; and
   a pump that is configured to be in communication with the piston chamber via a conduit and is configured to pump a sample diffused in an ambient gas into the adsorption cavity through the sample collection structure, the adsorption cavity being configured to adsorb the sample collected by the sample collection structure;
   wherein, the piston type adsorber is configured to be movable between a sample collecting position where the adsorption cavity is located outside the thermal desorption chamber and in communication with the sample collection structure so as to adsorb the sample collected by the sample collection structure and a sample desorbing position where the adsorption cavity is located inside the thermal desorption chamber so that the adsorbed sample is thermally desorbed in the thermal desorption chamber.

2. The sample injection device of claim 1, wherein
   the sample collection structure comprises a sample collection opening, a filter structure mounted over the sample collection opening, and a connection tube connecting the sample collection opening to the piston cylinder; and
   the piston cylinder comprises a cylinder body that is mounted to the thermal desorption chamber and is provided with a sampling connection gas nipple configured to be in communication with the piston chamber, and one end of the connection tube is configured to be mounted hermetically and detachably to the sampling connection gas nipple.

3. The sample injection device of claim 2, wherein a desiccant for adsorption of moisture in the collected sample is placed within the connection tube.

4. The sample injection device of claim 2, wherein at least a portion of the connection tube comprises a retractable hose.

5. The sample injection device of claim 4, wherein the piston type adsorber comprises a piston rod body and the adsorption cavity connected to a distal end of the piston rod body, and the adsorption cavity comprises a net-like structure filled with adsorbents therein.

6. The sample injection device of claim 5, wherein
   the piston rod body comprises a cooling passage and a plurality of through holes formed in a lower part of the piston rod body,
   the cooling passage is configured to be in direct communication with the ambient gas when the piston type adsorber is located at the sample collecting position, and in communication with the ambient gas via a cooling through hole formed in the piston cylinder when the piston type adsorber is located at the sample desorbing position, and
   the plurality of through holes are configured to be in communication with the cooling passage and the piston chamber.

7. The sample injection device of claim 1, wherein the piston type adsorber comprises a piston rod body and the adsorption cavity connected to a distal end of the piston rod body, and the adsorption cavity comprises a net-like structure filled with adsorbents therein.

8. The sample injection device of claim 7, wherein the adsorption cavity comprises an adsorption passage configured to be in communication with the sample collection structure to receive the collected sample when the piston type adsorber is located at the sample collecting position.

9. The sample injection device of claim 7, wherein the piston type adsorber further comprises a thermal insulation pad detachably connected to one end of the adsorption cavity away from the piston rod body.

10. The sample injection device of claim 7, wherein
    the piston rod body comprises a cooling passage and a plurality of through holes formed in a lower part of the piston rod body,
    the cooling passage is configured to be in direct communication with the ambient gas when the piston type adsorber is located at the sample collecting position, and in communication with the ambient gas via a cooling through hole formed in the piston cylinder when the piston type adsorber is located at the sample desorbing position, and
    the plurality of through holes are configured to be in communication with the cooling passage and the piston chamber.

11. The sample injection device of claim 7, further comprising a plurality of sealing rings provided around the piston type adsorber such that the piston type adsorber is hermetically accommodated within the piston cylinder.

12. The sample injection device of claim 1, wherein the piston cylinder comprises a guide rail provided within the thermal desorption chamber to guide a movement of the piston type adsorber within the thermal desorption chamber.

13. The sample injection device of claim 1, wherein the thermal desorption chamber comprises a chamber body and a liner provided on an inner wall of the chamber body, and an outer wall of the chamber body is covered with a heating structure.

14. The sample injection device of claim 13, wherein the thermal desorption chamber is further provided with a carrier gas inlet, a gas outlet and an analyzer interface.

15. The sample injection device of claim 1, further comprising a thermal insulation structure provided between the piston cylinder and the thermal desorption chamber.

16. A trace detection apparatus comprising:
    the sample injection device for sample collection and sample thermal desorption according to claim 1; and
    a sample analyzer connected to the sample injection device.

17. A method of collecting and desorbing a sample by using the sample injection device of claim 1, the method comprising steps of:
- positioning the piston type adsorber into the sample collecting position so that the adsorption cavity is in communication with the sample collection structure;
- pumping a sample diffused in the ambient gas into the adsorption cavity through the sample collection structure by starting up the pump;
- maintaining a temperature inside thermal desorption chamber at a constant high temperature by using a thermal desorption temperature-controlling system; and
- moving and positioning the piston type adsorber into the sample desorbing position so that the adsorption cavity is located within the thermal desorption chamber and the sample adsorbed within the adsorption cavity is thermally desorbed within the thermal desorption chamber at the high temperature.

18. The method of claim 17, wherein the step of pumping a sample diffused in the ambient gas into the adsorption cavity through the sample collection structure by starting up the pump comprises:
- keeping the pump working to continuously pump the sample and to pre-concentrate the sample within the adsorption cavity.

19. The method of claim 18, wherein during the sample adsorbed by the adsorption cavity being thermally desorbed within the thermal desorption chamber at the high temperature, the pump is operated to pump gas so that a portion of the piston type adsorber outside the thermal desorption chamber is kept at a room temperature.

20. The method of claim 17, wherein during the sample adsorbed by the adsorption cavity being thermally desorbed within the thermal desorption chamber at the high temperature, the pump is operated to pump gas so that a portion of the piston type adsorber outside the thermal desorption chamber is kept at a room temperature.

\* \* \* \* \*